United States Patent
Dang et al.

(10) Patent No.: US 11,813,101 B2
(45) Date of Patent: Nov. 14, 2023

(54) IMAGE QUALITY IMPROVED VIRTUAL NON-CONTRAST IMAGES GENERATED BY A SPECTRAL COMPUTED TOMOGRAPHY (CT) SCANNER

(71) Applicant: KONINKLIJKE PHILIPS N.V., Eindhoven (NL)

(72) Inventors: Hao Dang, Mayfieled Heights, OH (US); Shiyu Xu, Mayfieled Heights, OH (US); Chuanyong Bai, Solon, OH (US); Hui Wang, Beachwood, OH (US); Douglas B. McKnight, Cardon, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 664 days.

(21) Appl. No.: 16/965,225

(22) PCT Filed: Jan. 30, 2019

(86) PCT No.: PCT/EP2019/052157
§ 371 (c)(1),
(2) Date: Jul. 27, 2020

(87) PCT Pub. No.: WO2019/149711
PCT Pub. Date: Aug. 8, 2019

(65) Prior Publication Data
US 2020/0367844 A1    Nov. 26, 2020

Related U.S. Application Data

(60) Provisional application No. 62/624,415, filed on Jan. 31, 2018.

(51) Int. Cl.
*A61B 6/00* (2006.01)
*G06T 5/00* (2006.01)

(52) U.S. Cl.
CPC ............. *A61B 6/482* (2013.01); *G06T 5/009* (2013.01); *G06T 2207/10081* (2013.01);
(Continued)

(58) Field of Classification Search
CPC .................. A61B 6/482; G06T 5/009; G06T 2207/10081; G06T 2207/20081; G06T 2207/20084; G06T 2207/30004
See application file for complete search history.

(56) References Cited

U.S. PATENT DOCUMENTS

| 7,968,853 B2 | 6/2011 | Altman |
| 8,345,944 B2 | 1/2013 | Zhu |

(Continued)

FOREIGN PATENT DOCUMENTS

| CN | 106600568 A | 4/2017 |
| CN | 107516330 A | 12/2017 |

(Continued)

OTHER PUBLICATIONS

PCT International Search Report, International application No. PCT/EP2019/052157, dated May 3, 2019.

(Continued)

*Primary Examiner* — David P Porta
*Assistant Examiner* — Fani Polyzos Boosalis
(74) *Attorney, Agent, or Firm* — Larry Liberchuk

(57) ABSTRACT

A spectral computed tomography imaging system (102) includes a radiation source (112) configured to emit x-ray radiation and a detector array (114) configured to detect x-ray radiation and generate spectral data. The spectral imaging system further includes a memory (134) configured to store a virtual non-contrast image enhancing module (136) that includes computer executable instructions including a neural network trained to produce image quality enhanced virtual non-contrast images. The neural network is (Continued)

trained with training spectral data and training non-contrast-enhanced images generated from a non-contrast-enhanced scan. The spectral imaging system further includes a processor (132) configured to process the spectral data with the trained neural network to produce the image quality enhanced virtual non-contrast images.

18 Claims, 4 Drawing Sheets

(52) U.S. Cl.
CPC .............. *G06T 2207/20081* (2013.01); *G06T 2207/20084* (2013.01); *G06T 2207/30004* (2013.01)

(56) References Cited

U.S. PATENT DOCUMENTS

| | | |
|---|---|---|
| 8,442,184 B2 | 5/2013 | Forthmann |
| 10,970,887 B2 | 4/2021 | Wang |
| 2004/0264626 A1 | 12/2004 | Besson |
| 2011/0064292 A1 | 2/2011 | Chen |
| 2014/0133729 A1 | 5/2014 | Goshen |

FOREIGN PATENT DOCUMENTS

| | | | | |
|---|---|---|---|---|
| CN | 107530037 A | * | 1/2018 | .............. A61B 6/03 |
| JP | 2018089301 A | | 6/2018 | |
| WO | WO2009072056 A2 | | 6/2009 | |
| WO | WO2017215284 A1 | | 12/2017 | |

OTHER PUBLICATIONS

Mengheng T. et al., "A Neural Network-Based Method for Spectral Distortion Correction in Photon Counting X-Ray CT", Physics in Medicine and Biology, Institute Of Physics Publishing, Bristol GB, vol. 61, No. 16, Jul. 29, 2016.

Mahgerefteh S. et al., "Dual-Energy Derived Virtual Nonenhanced Computed Tomography Imaging: Current Status and Applications", Seminar Ultrasound CT MR, vol. 31, issue 4, pp. 321-327, Aug. 2010.

Song I. et al., "Virtual Non-Contrast CT Using Dual-Energy Spectral CT: Feasibility of Coronary Artery Calcium Scoring", Korean Journal of Radiology, May-Jun. 2016.

Tian S-F. et al., "Application of Computed Tomography Virtual Non contrast Spectral Imaging in Evaluation of Hepatic Metastases: A Preliminary Study", Chininese Medical Journal (Engl), vol. 128, issue 5, pp. 610-614, Mar. 5, 2015.

Lundin M. et al., "Virtual Non-Contrast Dual-Energy CT Compared to Single-Energy CT of the Urinary Tract: A Prospective Study", Vacta Radiologica, vol. 53, issue 6, pp. 689-694, 2012.

Chen H. et al., "Low-Dose CT Denoising with Convolutional Neural Network", 2017 IEEE 14th International Symposium on Biomedical Imaging, 2017.

Jiang X.Y. et al., "Evaluation of Virtual Non Contrast Images Obtained from Dual Energy CTA for Diagnosing Subarachnoid Hemorrhage", AJNR Am J Neuroradiol, 36, pp. 855-860, May 2015.

Gouk H.G.R. et al., "Fast Sliding Window Classification with Convolutional Neural Networks," IVNVZ '14 Proceedings of the 29th International Conference on Image and Vision Computing New Zealand, pp. 114-118, Nov. 19-21, 2014.

Long J. et al., "Fully Convolutional Networks for Semantic Segmentation." Proceedings of the IEEE Conference on Computer Vision and Pattern Recognition (CVPR), 2015.

Ronneberger O. et al., "U-Net: Convolutional Networks for Biomedical Image Segmentation", Medical Image Computing and Computer-Assisted Intervention (MICCAI), Springer, LNCS, vol. 9351: 234-241, 2015.

* cited by examiner

IMAGE QUALITY IMPROVED VIRTUAL NON-CONTRAST IMAGES GENERATED BY A SPECTRAL COMPUTED TOMOGRAPHY (CT) SCANNER

FIELD OF THE INVENTION

The following generally relates to imaging and more particularly to improving an image quality of virtual non-contrast images generated with data acquired with a spectral computed tomography (CT) scanner.

BACKGROUND OF THE INVENTION

A CT scanner generally includes a single broadband x-ray tube mounted on a rotatable gantry opposite a detector array. The x-ray tube rotates around an examination region located between the x-ray tube and the detector array and emits polychromatic radiation that traverses the examination region. The detector array detects radiation that traverses the examination region and generates projection data. The projection data is reconstructed to generate volumetric image data, which can be used to generate one or more two-dimensional images. The images include pixels represented in terms of gray scale values corresponding to relative radiodensity. These values reflect the attenuation characteristics of the scanned subject and generally show structure such as anatomical structures within the subject.

A contrast-enhanced CT scan includes scanning a subject that has been administered a radiocontrast agent. Procedures including a contrast-enhanced scan have also included a non-contrast-enhanced scan. For example, for coronary artery disease, contrast-enhanced images are useful to detect vessel narrowing and/or leakage, but are not well-suited to detect vessel calcification because of presence of iodine, and a separate non-enhanced scan is also performed for detecting vessel calcification. In another example, for renal masses, patients have undergone a non-contrast-enhanced scan and a contrast-enhanced nephrographic scan, where attenuation values between the non-contrast-enhanced and the contrast-enhanced nephrographic images are compared to determine whether a mass is enhancing. Unfortunately, performing two scans, instead of one, increases total patient x-ray radiation dose and scan time, and reduces patient throughput.

With such a CT scanner, the detected radiation also includes spectral information as the absorption of the radiation by the subject and/or object is dependent on the energy of the photons traversing therethrough. Such spectral information can provide additional information such as information indicative of the elemental or material composition (e.g., atomic number) of the tissue and/or material of the subject and/or object. Unfortunately, the projection data does not reflect the spectral characteristics as the signal output by the detector array is proportional to the energy fluence integrated over the energy spectrum. Such a CT scanner is also referred to herein as a non-spectral CT scanner. A CT scanner configured for spectral imaging leverages the spectral information. Such a CT scanner is referred to herein as a spectral CT scanner.

A spectral CT scanner takes advantage of the differences in energy-dependent attenuation properties of materials in the subject (e.g., bone, soft tissue, fat, injected contrast agent) to provide material-specific images through material decomposition. An example spectral CT scanner is configured for dual-energy in which projection data is acquired at two different (e.g., higher and lower) energy levels. Example dual-energy configurations include: 1) one x-ray tube emitting x-ray radiation at one energy level and two layers of x-ray detectors respectively detecting lower energy x-rays and higher energy x-rays; 2) one x-ray tube with fast kV-switching and a single-layer detector, and 3) two x-ray tube/single-layer detector pairs angularly offset (e.g., 90 degrees) from each other.

The material-specific images from a contrast-enhanced scan have been processed to generate "virtual" non-contrast (VNC) images. The VNC images represent an approximation of "true" non-contrast (TNC) images from a non-contrast scan. As such, a spectral CT scanner can generate both contrast-enhanced images and VNC images from a single contrast-enhanced scan. In one instance, this mitigates having to perform both a non-contrast-enhanced scan and a contrast-enhanced scan for studies requiring both types of scans. As a result, total patient x-ray radiation dose and scan time are reduced, and patient throughput can be increased.

However, the image quality of VNC images tends to be degraded relative to TNC images. For example, with VNC images the signal can become smaller than ground truth or even missing relative to TNC images. The literature provides an example where one kidney stone is present and another is missing in the same VNC images, where the TNC image includes both. Furthermore, VNC images tend to exhibit higher noise and more artifact relative to TNC images. Higher noise may lead to reduced sensitivity and an increased false-positive rate in detection. Examples of artifact includes beam hardening and rim artifact. Unfortunately, such degradation in image quality can affect diagnosis.

SUMMARY OF THE INVENTION

Aspects described herein address the above-referenced problems and others. In one aspect, a spectral imaging system includes a radiation source configured to emit x-ray radiation and a detector array configured to detect x-ray radiation and generate spectral data. The spectral imaging system further includes a memory configured to store a virtual non-contrast image enhancing module that includes computer executable instructions including a neural network trained to produce image quality enhanced virtual non-contrast images. The neural network is trained with training spectral data and training non-contrast-enhanced images generated from a non-contrast-enhanced scan. The spectral imaging system further includes a processor configured to process the spectral data with the trained neural network to produce the image quality enhanced virtual non-contrast images.

In another aspect, a spectral imaging system includes a radiation source configured to emit x-ray radiation and detector array configured to detect x-ray radiation and generate spectral data. The spectral imaging system further includes a memory configured to store a virtual non-contrast image enhancing module that includes computer executable instructions including a neural network. The spectral imaging system further includes a processor configured to train the neural network to produce image quality enhanced virtual non-contrast images with training spectral data and training non-contrast-enhanced images generated from a non-contrast-enhanced scan.

In another aspect, a computer readable storage medium is encoded with computer readable instructions, which, when executed by a computer processor of a computing system, causes the computer processor to: emit x-ray radiation with a radiation source, detect emitted x-ray radiation with a detector array and generate a spectral data, train a neural network trained to produce image quality enhanced virtual non-contrast images, and process the spectral data with the trained neural network to produce the image quality enhanced virtual non-contrast images.

Those skilled in the art will recognize still other aspects of the present application upon reading and understanding the attached description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

The following describes an approach to improve an image quality of virtual non-contrast (VNC) images generated with data acquired with a spectral CT scanner during a contrast-enhanced spectral scan. Contrast-enhanced dual-energy spectral data, such as low and high kVp data from a spectral CT scanner, are reconstructed to generate contrast-enhanced low and high kVp images, which are decomposed to generate spectral images, including the VNC image. The two kVp images will include beam hardening artifacts, e.g., due to the contrast (i.e. photoelectric absorption). Even when beam hardening compensation is applied during reconstruction of the kVp images, the two kVp images will likely include residual beam hardening artifacts. The residual beam hardening artifacts can be further reduced during the decomposition, but the resulting VNC image will still include residual beam hardening artifacts, which can reduce image quality.

In an approach described herein, a neural network is trained with a set of training spectral images as input and a set of training TNC images as reference data. During training, the neural network learns to map the set of training spectral images to the set of training TNC images. In one instance, the set of training spectral images includes spectral images with different noise levels and the set of training TNC images as reference data includes low noise TNC images. The mapping is non-linear such that the residual beam-hardening artifacts in the input VNC images are further reduced and/or do not show in the final VNC images, and noise in the input VNC images is reduced in the final VNC images. As such, this approach can produce contrast-enhanced images and VNC images with an image quality similar or equivalent to TNC images.

Figure 1:
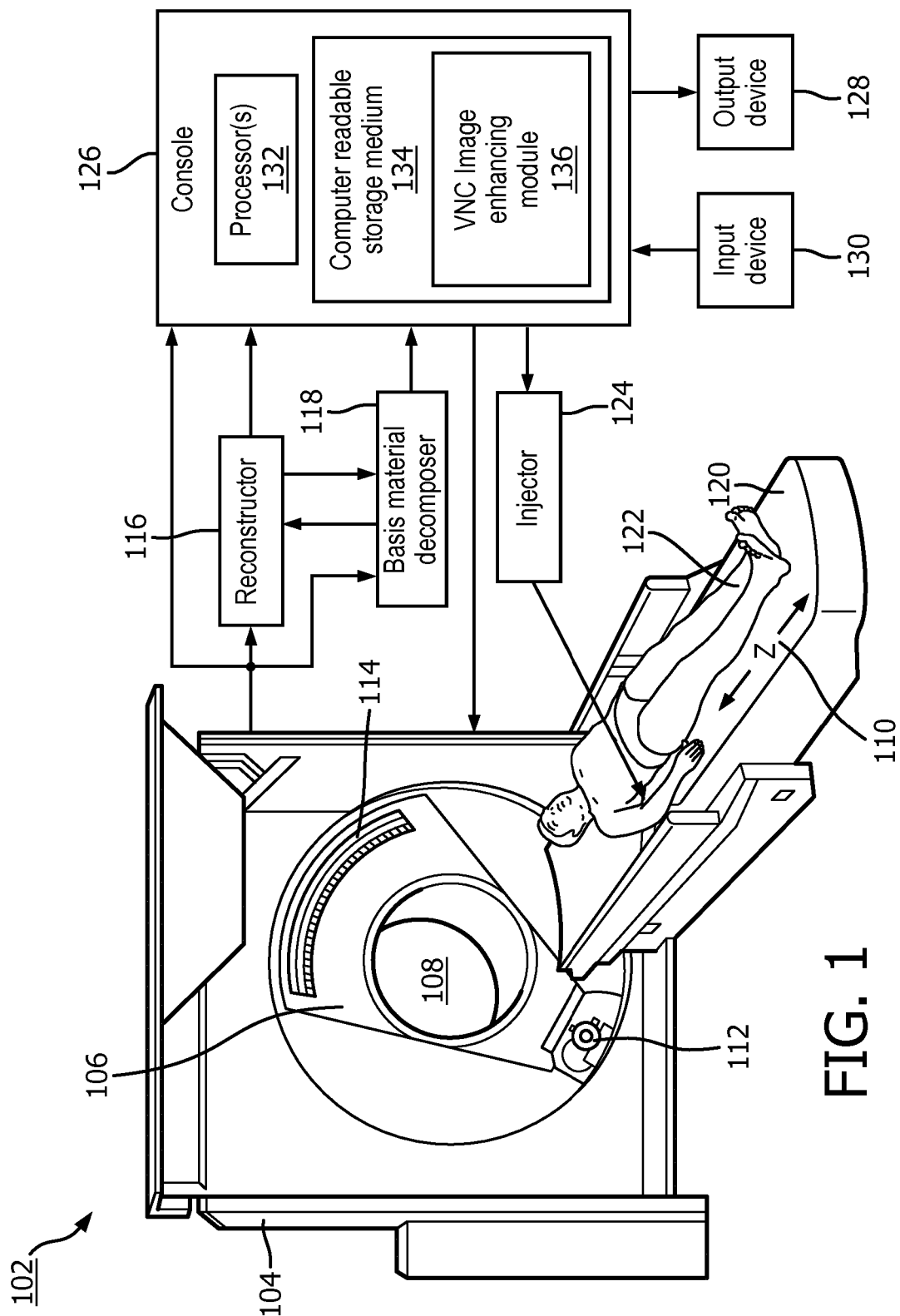
FIG. 1 schematically illustrates an example spectral computed tomography scanner with a VNC image enhancing module that includes a neural network trained to improve an image quality of VNC images generated by the scanner.

FIG. 1 schematically illustrates an example computed tomography (CT) scanner 102 configured for spectral CT imaging, e.g., multi-energy imaging such as dual-energy imaging. The CT scanner 102 includes a stationary gantry 104 and a rotating gantry 106, which is rotatably supported by the stationary gantry 104 and rotates around an examination region 108 (and a portion of an object or subject therein) about a longitudinal or z-axis 110.

A radiation source 112, such as an x-ray tube, is supported by and rotates with the rotating gantry 106 around the examination region 108. The radiation source 112 emits x-ray radiation that is collimated to form a generally fan, wedge, or cone shaped x-ray radiation beam that traverses the examination region 108. In one instance, the radiation source 112 is a single x-ray tube configured to emit broadband (polychromatic) radiation for a single selected peak emission voltage (kVp) of interest.

In another instance, the radiation source 112 is configured to switch between at least two different emission voltages (e.g., 70 keV, 100 keV, 120 keV, etc.) during a scan. In yet another instance, the radiation source 112 includes two or more x-ray tubes angular offset on the rotating gantry 104 with each configured to emit radiation with a different mean energy spectrum. U.S. Pat. No. 8,442,184 B2 describes a system with kVp switching and multiple x-ray tubes, and is incorporated herein by reference in its entirety.

A radiation sensitive detector array 114 subtends an angular arc opposite the radiation source 112 across the examination region 108. The detector array 114 includes one or more rows of detectors that are arranged with respect to each other along the z-axis direction and detects radiation traversing the examination region 108. For a contrast-enhanced scan, the detector array 114 generates contrast-enhanced spectral projection data (line integrals) such as contrast-enhanced high energy projection data and contrast-enhanced low energy projection data.

In this example, the detector array 114 includes an energy-resolving detector such as a multi-layer scintillator/photosensor detector (e.g., U.S. Pat. No. 7,968,853 B2, which is incorporated herein by reference in its entirety). In a variation, the detector array 114 includes a photon counting (direct conversion) detector (e.g., WO 2009/072056 A2, which is incorporated herein by reference in its entirety). In these instances, the radiation source 112 includes the broadband, kVp switching and/or multiple X-ray tube radiation sources. Where the detector array 114 includes a non-energy-resolving detector, the radiation source 112 includes kVp switching and/or multiple X-ray tube radiation sources.

A reconstructor 116 processes the contrast-enhanced spectral projection data and generates contrast-enhanced spectral volumetric image data such as contrast-enhanced high energy volumetric image data and contrast-enhanced low energy volumetric image data. The reconstructor 116 can also generate contrast-enhanced non-spectral volumetric image data, e.g., by first combining the high energy projection data and the low energy projection data and then reconstructing the combined projection data and/or by combining the high energy volumetric image data and low energy volumetric image data. Spectral and non-spectral images can be derived therefrom. The reconstructor 116 can be implemented with a processor such as a central processing unit (CPU), a microprocessor, etc.

In the illustrated embodiment, a basis material decomposer 118 decomposes the contrast-enhanced projection data (projection domain decomposition) and/or the contrast-enhanced spectral volumetric image data and/or images (image domain decomposition) into basis components. When configured for projection domain decomposition, the reconstructor 116 reconstructs the projection data basis components to generate basis component volumetric image data and/or images such as VNC volumetric image data and/or images. When configured for image domain decomposition, the basis material decomposer 118 decomposes contrast-enhanced spectral volumetric image data and/or images into basis component volumetric image data and/or images such as VNC volumetric image data and/or images. In a variation, separate basis material decomposers are used for projection and image domain decomposition. In another variation, the basis material decomposer 118 is omitted or not employed.

With one approach, the basis material decomposer 118 employs two material decomposition algorithms, each assuming a water-iodine basis material pair or a calcium-iodine basis material pair, to generate VNC images without iodine. Another approach is to perform an N-dimensional cluster analysis to decompose the images into components such as iodine or other materials including soft tissue, calcium, etc. Other examples are described in Song, et al., "Virtual Non-Contrast CT Using Dual-Energy Spectral CT: Feasibility of Coronary Artery Calcium Scoring," Korean J Radiol 2016; 17(3):321-329, and US 2014/0133729 A1, filed Jan. 13, 2014, and entitled "Image Processing for Spectral CT," which is incorporated herein by reference in its entirety. The decomposer 118 can be implemented with a processor or the like.

A subject support 120, such as a couch, supports a subject or object (e.g., a phantom) 122 in the examination region 108. The subject support 120 is movable in coordination with performing an imaging procedure so as to guide the subject or object with respect to the examination region 108 for loading, scanning, and/or unloading the subject or object.

An injector 124 is configured to inject or administer a material such as one or more (e.g., iodine) contrast agents to the subject or object 122 to be scanned for a perfusion scan. A contrast agent can additionally or alternatively be manually administered by a clinician or the like. Where the contrast agent is manually administered to the subject or object 122, the injector 124 can be omitted.

An operator console 126 includes a human readable output device 128 such as a display monitor, a filmer, etc. and an input device 130 such as a keyboard, mouse, etc. The console 126 further includes a processor 132 (e.g., a CPU, a microprocessor, etc.) and computer readable storage medium 134 (which excludes transitory medium) such as physical memory. In the illustrated embodiment, the computer readable storage medium 134 includes a VNC image enhancing module 136.

The illustrated VNC image enhancing module 136 includes computer executable instructions for processing VNC images to produce improved image quality VNC image (image quality enhanced virtual non-contrast images) similar or equivalent to TNC images generated from a non-contrast-enhanced scan. As described in greater detail below, the instructions include a neural network trained with training spectral data and TNC images. As such, as discussed above, the spectral CT scanner 102 can produce contrast-enhanced images and VNC images with image quality diagnostically similar or equivalent to TNC images generated from a non-contrast-enhanced scan using data acquired with a single contrast-enhanced scan.

FIGS. 2-7 schematically illustrate different embodiments for training the neural network. In these embodiments, by using training data sets with data acquired with different contrast delivery, the neural network is trained to take into account differences in the delivery of contrast material in the input data. In one example, the training data sets are constructed such that the distribution of the data feature (i.e., contrast delivery) well represents the distribution of the data feature in real clinical scenarios. The training data sets can come from both real clinical scans and simulation. An advantage of a simulation is that contrast delivery can be controlled in every data set (including contrast-enhanced spectral CT data and TNC images) and thereby a large number of data sets can be generated that strictly follow a presumed distribution of the data feature. In another instance, the input and training data can be acquired such that contrast delivery is consistent across the data.

Figure 2:
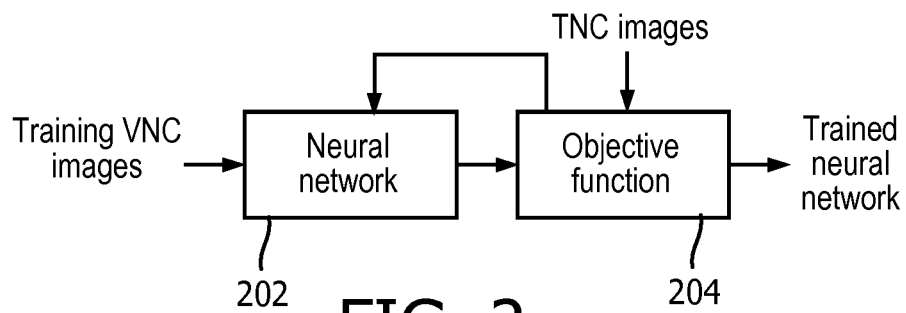
FIG. 2 schematically illustrates an example of training the neural network with a set of training VNC images and a set of training TNC images.

FIG. 2 schematically illustrates example training of a neural network 202 with training VNC images generated using material decomposition and training TNC images from a non-contrast-enhanced CT scan. Parameters of the neural network are updated and converge through a number of iterations using an objective function 204. The objective function 204, in one instance, includes a mathematical function that minimizes an error between the VNC volumetric image data or images output by the neural network 202 and TNC images, e.g., based on a mean squared and/or other difference between the VNC volumetric image data or images output by the neural network 202 and TNC images. In this instance, the parameters are updated until the error falls below of predetermined threshold. Other stopping criteria include a predetermined number of iterations, a predetermined time duration, etc.

Figure 3:
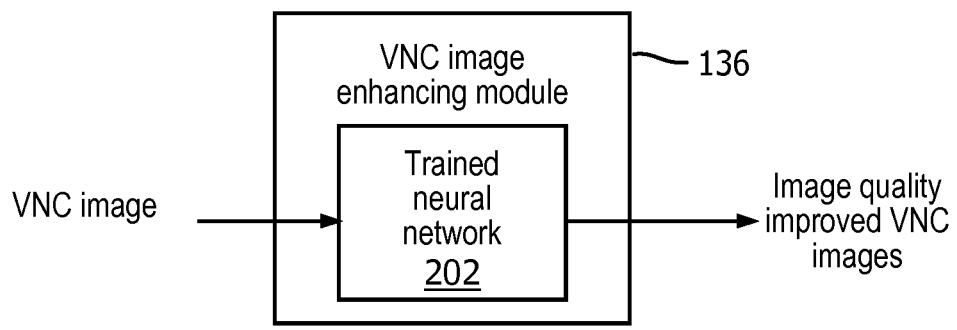
FIG. 3 schematically illustrates an example of employing the trained neural network of FIG. 2 with VNC images generated by the spectral computed tomography scanner to produce image quality improved VNC images.

FIG. 3 schematically illustrates an embodiment in which the VNC image enhancing module 136 includes the trained neural network 202 of FIG. 2. The trained neural network 202 receives the VNC images (which contain high noise and/or artifacts relative to TNC images) generated by the basis material decomposer 118 (FIG. 1) and outputs image quality improved VNC images, which includes VNC images with less noise and/or artifact than the input VNC images and which has sufficient image quality for diagnosis.

Figure 4:
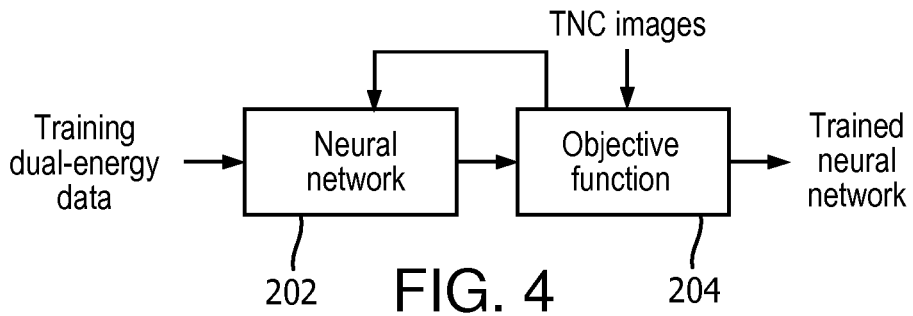
FIG. 4 schematically illustrates an example of training the neural network with a set of training dual-energy images and the set of training TNC images.
Figure 5:
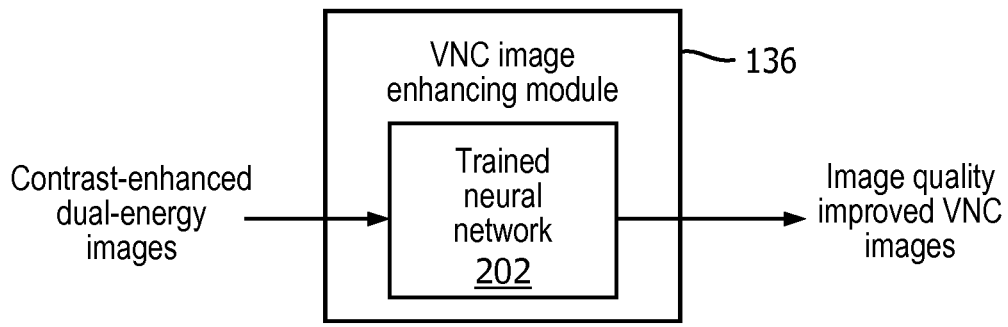
FIG. 5 schematically illustrates an example of employing the trained neural network of FIG. 4 with contrast-enhanced dual-energy images generated by the spectral computed tomography scanner to produce image quality improved VNC images.

FIG. 4 schematically illustrates a variation of FIG. 2 in which the input to the neural network 202 is training dual-energy (high and low energy) images. FIG. 5 schematically illustrates an embodiment in which the VNC image enhancing module 136 includes the neural network 202 trained in FIG. 4. The trained neural network 202 receives contrast-enhanced dual-energy images generated by the reconstructor 116 (FIG. 1) and outputs image quality improved VNC images. For this variation, the basis material decomposer 118 is either omitted from the system 102 of FIG. 1 or not utilized.

For this variation, the neural network 202 handles the material decomposition as it is capable of performing non-linear mapping of data, and material decomposition often involves solving polynomial equations (e.g., for high energy and low energy) after approximations. By using the neural network 202 for material decomposition, the noise in the basis material images can be lower than the noise from conventional material decomposition, e.g., because conventional material decomposition only uses measured data on one detector pixel or reconstructed value of one image voxel at a time, but neural network uses a small patch, which includes more than one pixel or voxel.

In general, projection data includes unique spectral information hidden in the data. For example, even though the attenuation along a certain ray path can be the same for both high-Z, low density and low-Z, high density objects, the physical effects, i.e., Compton scatter and photoelectric absorption, can be different with low-Z, high density objects leading to more Compton scatter, and these differences are hidden in the acquired raw projection data. Another example is that there are more beam hardening artifacts for high-Z materials relative to low-Z materials. These differences are reduced and/or removed and do not show up in the reconstructed volumetric image data, e.g., to effective scatter correction, beam-hardening compensation, etc.

In a variation, corrections that remove spectral information, such as a scatter correction and/or beam hardening, are omitted from the reconstruction. For example, in another instance, the neural network 202 of FIGS. 2-3 is trained with VNC images generated from volumetric image data that was reconstructed without using a correction, such as scatter correction and/or beam-hardening compensation, that removes the unique spectral information, and/or the neural network 202 of FIGS. 4-5 is trained with high and low energy images reconstructed without using a correction, such as scatter correction and/or beam-hardening compensation, that removes the unique spectral information. This allows the training to take into account the unique spectral information.

Figure 6:
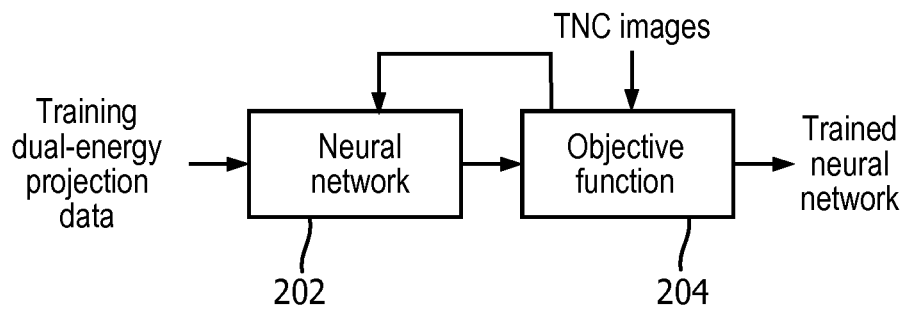
FIG. 6 schematically illustrates an example of training the neural network with a set of training dual-energy projection data and the set of TNC images.
Figure 7:
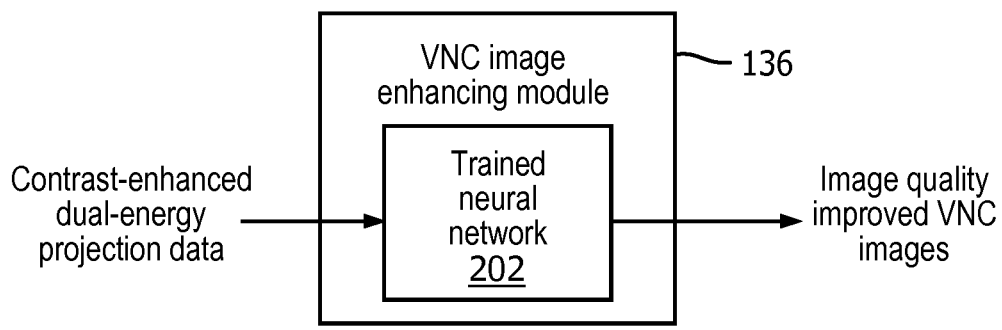
FIG. 7 schematically illustrates an example of employing the trained neural network of FIG. 6 with contrast-enhanced dual-energy projection data generated by the spectral computed tomography scanner to produce image quality improved VNC images.

FIG. 6 schematically illustrates a variation of FIG. 2 in which the input to the neural network 202 is training dual-energy (high and low energy) projection data. FIG. 7 schematically illustrates an embodiment in which the VNC image enhancing module 136 includes the neural network 202 trained in FIG. 6. The trained neural network 202 receives contrast-enhanced dual-energy projection data generated by the detector array 114 (FIG. 1) and outputs image quality improved VNC images. For this variation, the basis material decomposer 118 is either omitted from the system 102 of FIG. 1 or not utilized.

A variation includes two of the three embodiments described in FIGS. 2-7. For example, one variation includes the neural network of FIGS. 2 and 4. Another variation includes the neural network of FIGS. 2 and 6. Another variation includes the neural network of FIGS. 4 and 6. Another variation includes all three of the three embodiments described in FIGS. 2-7. Another variation includes a single neural network trained with different types of training such as the training data in FIGS. 2 and 4, 2 and 6, 2 and 6, or 2, 4 and 6. These variations can be employed with the input data of FIGS. 3, 5 and/or 7 to image quality improved VNC images.

Examples of suitable neural networks are described in Gouk, et al., "Fast Sliding Window Classification with Convolutional Neural Networks," IVNVZ '14 Proceedings of the 29th International Conference on Image and Vision Computing New Zealand, Pages 114-118, Nov. 19-21, 2014, "Fully convolutional networks for semantic segmentation," Proceedings of the IEEE Conference on Computer Vision and Pattern Recognition, 2015, and Ronneberger, et al., "U-Net: Convolution Networks for Biomedical Image Segmentation," Medical Image Computing and Computer-Assisted Intervention (MICCAI), Springer, LNCS, Vol. 9351: 234-241, 2015.

Figure 8:
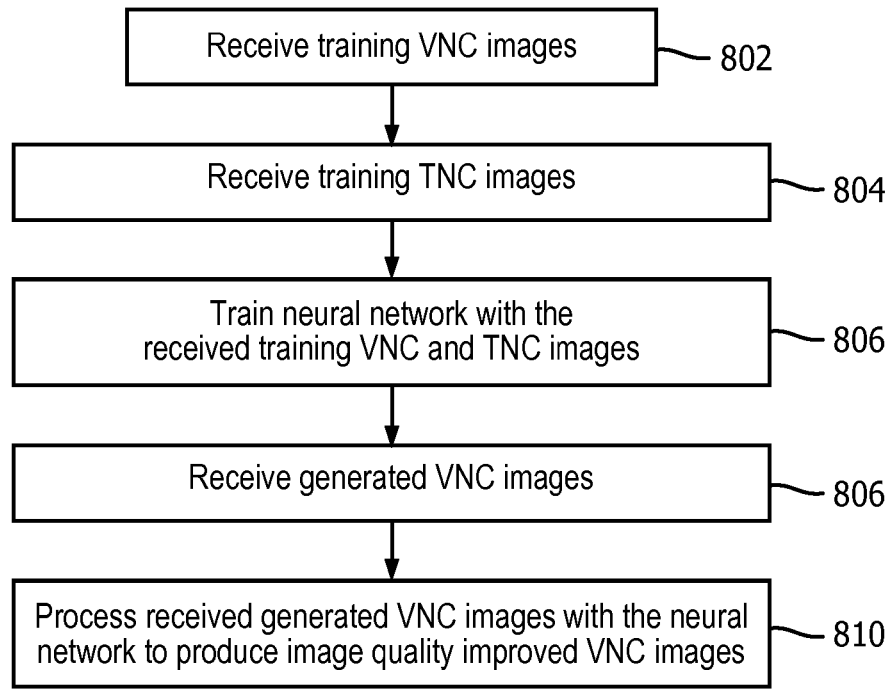
FIG. 8 illustrates an example method for training a neural network with training VNC and TNC images and employing the trained neural network to produce image quality improved VNC images.

FIG. 8 illustrates an example method in accordance with an embodiment herein.

It is to be appreciated that the ordering of the acts in the method is not limiting. As such, other orderings are contemplated herein. In addition, one or more acts may be omitted, and/or one or more additional acts may be included.

At 802, a set of training VNC images is received, as described herein and/or otherwise.

At 804, a set of training TNC images is received, as described herein and/or otherwise.

At 806, the set of training VNC images and the set of training TNC images are employed to train a neural network, as described herein and/or otherwise.

At 808, VNC images are received, as described herein and/or otherwise.

At 810, the received VNC images are processed with the trained neural network to produce image quality improved VNC images.

Figure 9:
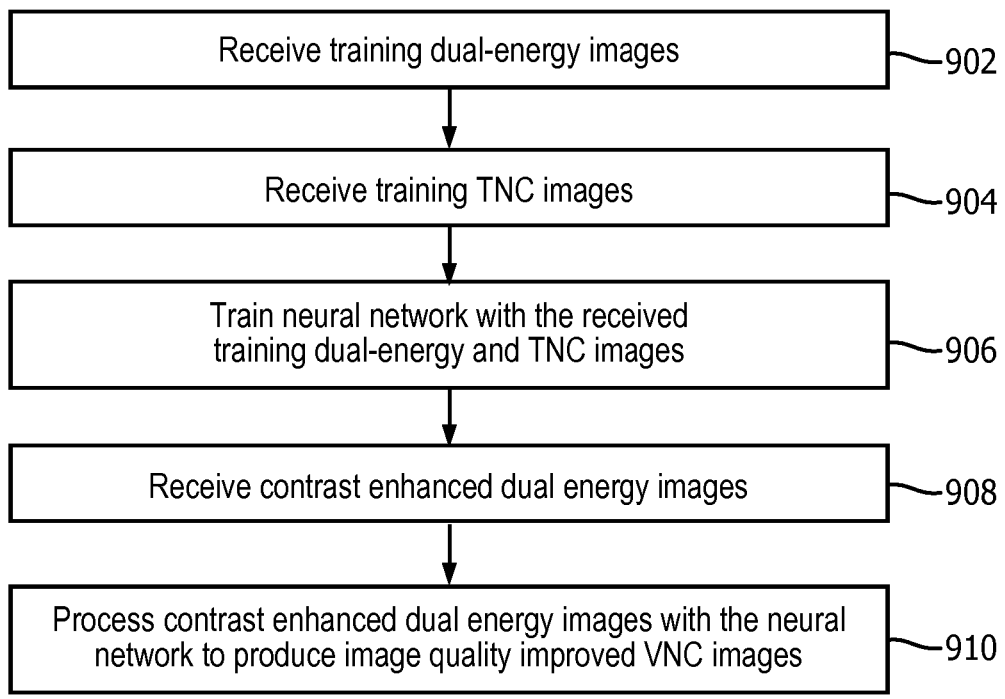
FIG. 9 illustrates an example method for training a neural network with training dual-energy and the TNC images and employing the trained neural network to produce image quality improved VNC images.

FIG. 9 illustrates another example method in accordance with an embodiment herein.

It is to be appreciated that the ordering of the acts in the method is not limiting. As such, other orderings are contemplated herein. In addition, one or more acts may be omitted, and/or one or more additional acts may be included.

At 902, a set of training dual-energy images is received, as described herein and/or otherwise.

At 904, a set of training TNC images is received, as described herein and/or otherwise.

At 906, the set of training dual-energy images and the set of training TNC images are employed to train a neural network, as described herein and/or otherwise.

At 908, contrast-enhanced dual-energy images are received, as described herein and/or otherwise.

At 910, the contrast-enhanced dual-energy images are processed with the trained neural network to produce image quality improved VNC images.

Figure 10:
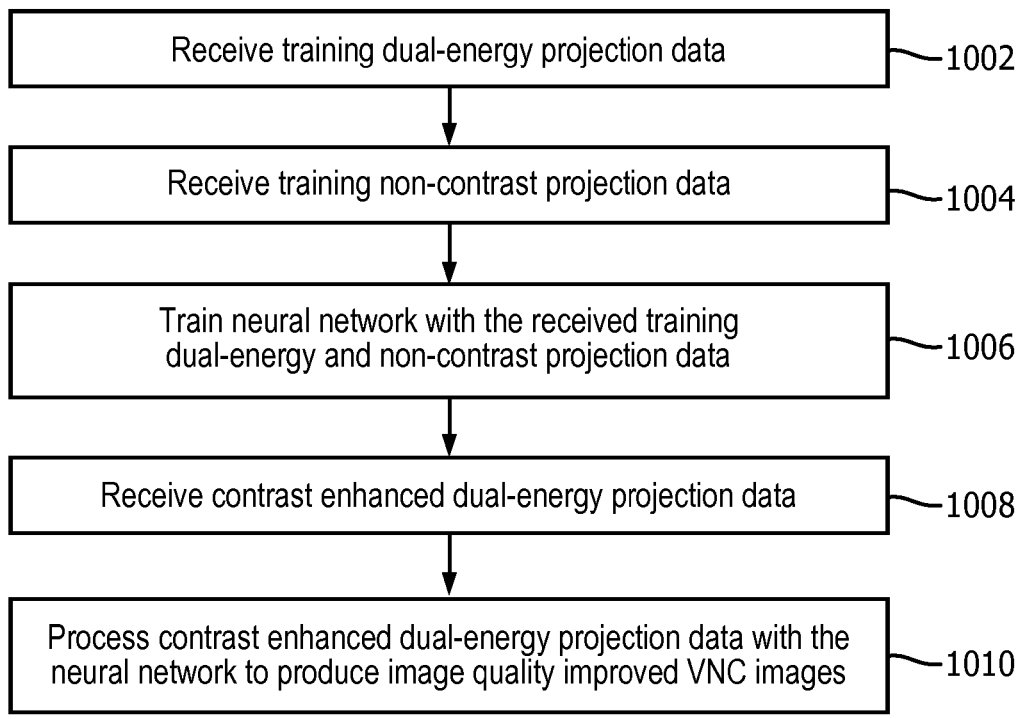
FIG. 10 illustrates an example method for training a neural network with training dual-energy projection data and the TNC images and employing the trained neural network to produce image quality improved VNC images.

FIG. 10 illustrates another example method in accordance with an embodiment herein.

It is to be appreciated that the ordering of the acts in the method is not limiting. As such, other orderings are contemplated herein. In addition, one or more acts may be omitted, and/or one or more additional acts may be included.

At 1002, a set of training dual-energy projection data is received, as described herein and/or otherwise.

At 1004, a set of training TNC images is received, as described herein and/or otherwise.

At 1006, the set of training dual-energy projection data and the set of training TNC images are employed to train a neural network, as described herein and/or otherwise.

At 1008, contrast-enhanced dual-energy projection data is received, as described herein and/or otherwise.

At 1010, the contrast-enhanced dual-energy projection data is processed with the trained neural network to produce image quality improved VNC images.

The above may be implemented by way of computer readable instructions, encoded or embedded on computer readable storage medium, which, when executed by a computer processor(s), cause the processor(s) to carry out the described acts. Additionally, or alternatively, at least one of the computer readable instructions is carried by a signal, carrier wave or other transitory medium, which is not computer readable storage medium.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A spectral computed tomography imaging system, comprising:
    a radiation source configured to emit x-ray radiation;
    a detector array configured to detect the x-ray radiation and generate contrast-enhanced multi-energy spectral projection data;
    a memory configured to store a virtual non-contrast image enhancing module that includes computer executable instructions including a neural network trained to produce image quality enhanced virtual non-contrast images,
    wherein the neural network is trained with training contrast-enhanced multi-energy spectral projection data generated from a spectral scan and training non-contrast-enhanced images generated from a non-contrast-enhanced scan; and
    a processor configured to process the contrast-enhanced multi-energy spectral projection data with the trained neural network to produce the image quality enhanced virtual non-contrast images.

2. The system of claim 1, wherein the neural network is configured to update its parameters to reduce an error between virtual non-contrast images generated from the training contrast-enhanced multi-energy spectral projection data and the training non-contrast-enhanced images.

3. The system of claim 1, further comprising:
    a reconstructor configured to reconstruct the contrast-enhanced multi-energy spectral projection data and generate contrast-enhanced multi-energy spectral images,
    wherein the processor is further configured to process the contrast-enhanced multi-energy spectral images with the trained neural network to produce the image quality enhanced virtual non-contrast images.

4. The system of claim 3, wherein the contrast-enhanced multi-energy training spectral projection data includes contrast-enhanced multi-energy spectral images generated from the spectral scan, and the neural network is configured to update its parameters to reduce an error between virtual non-contrast images generated from the training contrast-enhanced multi-energy spectral images and the training non-contrast-enhanced images.

5. The system of claim 3, further comprising:
    a basis material decomposer configured to process the contrast-enhanced multi-energy spectral images to produce initial virtual non-contrast images,
    wherein the processor is further configured to process the initial virtual non-contrast images with the trained neural network to produce the image quality enhanced virtual non-contrast images.

6. The system of claim 5, further comprising:
    a basis material decomposer configured to process the contrast-enhanced multi-energy spectral projection data to produce virtual non-contrast spectral projection data; and
    a reconstructor configured to reconstruct the virtual non-contrast spectral projection data to produce initial virtual non-contrast images;
    wherein the processor is further configured to process the initial virtual non-contrast images with the trained neural network to produce the image quality enhanced virtual non-contrast images.

7. The system of claim 5, wherein the training contrast-enhanced multi-energy spectral data generated from the spectral scan is processed to generate virtual non-contrast-enhanced images generated from the spectral scan, and the neural network is configured to update its parameters to reduce an error between virtual non-contrast images generated from the training virtual non-contrast-enhanced images and the training non-contrast-enhanced images.

8. A spectral computed tomography imaging method, comprising:
    emitting x-ray radiation;
    detecting the x-ray radiation and generating contrast-enhanced multi-energy spectral projection data;
    storing a virtual non-contrast image enhancing module that includes computer executable instructions including a neural network; and
    training the neural network with training contrast-enhanced multi-energy spectral projection data generated from a spectral scan and training non-contrast-enhanced images generated from a non-contrast-enhanced scan to produce image quality enhanced virtual non-contrast images.

9. The method of claim 8, wherein the neural network is configured to update its parameters to reduce an error between virtual non-contrast images generated from the training contrast-enhanced multi-energy spectral projection data and the training non-contrast-enhanced images.

10. The method of claim 9, wherein the spectral data includes multi-energy spectral projection data, and further comprising processing the multi-energy spectral projection data with the trained neural network to produce the image quality enhanced virtual non-contrast images.

11. The method of claim 8, wherein the training contrast-enhanced spectral data includes contrast-enhanced multi-energy spectral images generated from the spectral scan, and the neural network is configured to update its parameters to reduce an error between virtual non-contrast images generated from the training contrast-enhanced multi-energy spectral images and the training non-contrast-enhanced images.

12. The method of claim 11, wherein the spectral data includes multi-energy spectral projection data, and further comprising:

reconstructing the multi-energy spectral projection data and generating multi-energy spectral images, wherein the multi-energy spectral images are processed with the trained neural network to produce the image quality enhanced virtual non-contrast images.

13. The method of claim 8, wherein the training spectral contrast-enhanced data generated from the spectral scan is processed to generate virtual non-contrast-enhanced images generated from the spectral scan, and the neural network is configured to update its parameters to reduce an error between virtual non-contrast images generated from the training virtual non-contrast-enhanced images and the training non-contrast-enhanced images.

14. The method of claim 13, further comprising:

reconstructing the contrast-enhanced multi-energy spectral projection data and generating contrast-enhanced multi-energy spectral images; and processing the contrast-enhanced multi-energy spectral images to produce initial virtual non-contrast images, wherein the initial virtual non-contrast images are processed with the trained neural network to produce the image quality enhanced virtual non-contrast images.

15. The method of claim 13, further comprising:

processing the contrast-enhanced multi-energy spectral images to produce virtual non-contrast spectral projection data; and reconstructing the virtual non-contrast spectral projection data to produce initial virtual non-contrast images;

wherein the initial virtual non-contrast images are processed with the trained neural network to produce the image quality enhanced virtual non-contrast images.

16. A non-transitory computer readable storage medium encoded with computer readable instructions, which, when executed by a processor of a computing system, cause the processor to:

emit x-ray radiation with a radiation source;

detect emitted x-ray radiation with a detector array and generate a contrast-enhanced spectral projection data;

train a neural network trained to produce image quality enhanced virtual non-contrast images, wherein the neural network is trained with training contrast-enhanced multi-energy spectral projection data generated from a spectral scan and training non-contrast-enhanced images generated from a non-contrast-enhanced scan; and process the spectral data with the trained neural network to produce the image quality enhanced virtual non-contrast images.

17. The non-transitory computer readable storage medium of claim 16, wherein the processor trains the neural network using training data having a distribution of a contrast delivery that represents a distribution of a contrast delivery from patient scans.

18. The non-transitory computer readable storage medium of claim 16, wherein the processor trains the neural network using simulated training data having a user determined distribution of a contrast delivery of interest.

* * * * *